US009688652B2

(12) United States Patent
Jackson et al.

(10) Patent No.: US 9,688,652 B2
(45) Date of Patent: *Jun. 27, 2017

(54) HYDROGENATION OF CATMINT OIL

(71) Applicant: E I DU PONT DE NEMOURS AND COMPANY, Wilmington, DE (US)

(72) Inventors: Scott Christopher Jackson, Wilmington, DE (US); Leo Ernest Manzer, Wilmington, DE (US); Henry Max Schleinitz, Dennis, MA (US); Mark A Scialdone, West Grove, PA (US); Keith W Hutchenson, Lincoln University, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/731,860

(22) Filed: Jun. 5, 2015

(65) Prior Publication Data

US 2015/0266846 A1   Sep. 24, 2015

Related U.S. Application Data

(62) Division of application No. 14/034,857, filed on Sep. 24, 2013, now Pat. No. 8,952,182, which is a division of application No. 12/519,582, filed as application No. PCT/US2007/025988 on Dec. 20, 2007, now Pat. No. 8,552,210.

(60) Provisional application No. 60/876,569, filed on Dec. 21, 2006.

(51) Int. Cl.
C07D 311/02     (2006.01)
C07D 311/94     (2006.01)

(52) U.S. Cl.
CPC ................. C07D 311/94 (2013.01)

(58) Field of Classification Search
CPC .................................................... C07D 311/94
USPC .......................................................... 549/283
See application file for complete search history.

(56) References Cited

U.S. PATENT DOCUMENTS

| 4,062,937 | A  | 12/1977 | Rea |
| 4,416,881 | A  | 11/1983 | McGovern |
| 4,496,467 | A  | 1/1985  | Munteanu |
| 4,869,896 | A  | 9/1989  | Coulston |
| 4,913,893 | A  | 4/1990  | Varco |
| 6,462,015 | B1 | 10/2002 | Weiss |
| 6,524,605 | B1 | 2/2003  | Coats |
| 6,673,756 | B2 | 1/2004  | Sonnenberg |
| 7,067,677 | B2 | 6/2006  | Manzer |
| 7,232,844 | B2 | 6/2007  | Hallahan |
| 7,820,145 | B2 | 10/2010 | Tamarkin |
| 8,558,015 | B2 * | 10/2013 | Fisher ............ A01N 43/16 549/283 |
| 2003/0225290 | A1 | 12/2003 | Manzer |
| 2004/0024054 | A1 | 2/2004  | Haenke |
| 2005/0112166 | A1 | 5/2005  | Hallahan |
| 2005/0244441 | A1 | 11/2005 | Courtois |
| 2006/0223878 | A1 | 10/2006 | Scialdone |
| 2007/0077262 | A1 | 4/2007  | Scialdone |
| 2007/0264297 | A1 | 11/2007 | Scialdone |
| 2008/0305135 | A1 | 12/2008 | Kroepke |
| 2010/0034906 | A1 | 2/2010  | Gonzalez |
| 2010/0092404 | A1 | 4/2010  | Hutchenson |
| 2010/0145077 | A1 | 6/2010  | Jackson |
| 2010/0145078 | A1 | 6/2010  | Fisher |
| 2010/0168447 | A1 | 7/2010  | Hutchenson |
| 2010/0261915 | A1 | 10/2010 | Gonzalez |

FOREIGN PATENT DOCUMENTS

WO    2005034626    4/2005

OTHER PUBLICATIONS

Tanimori et. al., Total Synthesis of (+) Dihydronepetalactone, Agric. Biol. Chem., 1991, vol. 55:1181-11832.
Fleming et. al., Sterocontrol in Organic Synthesis Using Silicon-Containing Compounds, a Synthesis of (+) Dihydronepetalactone Using the Se2 Reaction of an Allysilane, J. Chem. Soc., Perkin Trans, 1998, vol. 1:2645-2649.
Wolinsky et. al., Syntheses of the Dihydronepetalactones, J. Org. Chem., 1972, vol. 37:3376-3378.
Jefson et. al., Chemical Defense of a Rove Beetle, Journal of Chemical Ecology, 1983, vol. 9:150-180.
G.W.K. Cavill et. al., Defensive and Other Secretions of the Australlian Cocktail Ant, *Iridomyrmex nitidiceps*, Tetrahedron, 1982, vol. 38:1931-1938.
Chris Peterson et. al., Insect Repellents—Past, Present and Future, Pesticide Outlook, Aug. 2001.
Depooter et. al., The Essential Oils Five *Nepeta* Species. A Preliminary Evaluation of Their Use in Chemotaxonomy by Cluster Analysis, Flavour and Fragrance Journal, 1988, vol. 3:155-159.
Handjieva et. al., Constituents of Essential Oils From Nepeta cataria L., N. Grandiflora M.B. and N. nuda L., J. Essential Oil Res., 1996, vol. 8:639-643.
T. Eisner, Science, 1964, vol. 146: 1318-1320.
Regnier et al., Studies on the Composition of the Essential Oils of Three *Nepeta* Species, Phytochemistry, 1967, vol. 6, pp. 1281-1289.
International Search Report, PCT/US2007/025988, Dated Jun. 5, 2008.
Regnier et al., Nepetalactone and Epinepetalactone From Nepeta cataria, Phytochemistry, 1967, vol. 6, pp. 1271-1280.

(Continued)

*Primary Examiner* — Nizal Chandrakumar
(74) *Attorney, Agent, or Firm* — Linda D. Birch

(57) ABSTRACT

Disclosed are methods for treating catmint oil. The process allows the separation of sulfur-containing compounds from the catmint oil. The treated catmint oil can be used for the production of hydrogenated catmint oil, which is enriched in the insect repellent, dihydronepetalactone.

6 Claims, No Drawings

(56) References Cited

OTHER PUBLICATIONS

Navarro et al., Hydrogenation of Aromatics on Sulfur Resistant PTPD Bimetallic Catalysts, Journal of Catalysis, 2000, vol. 189, pp. 184-194.

Yang et al., Shape Selective and Hydrogen Spillover Approach in the Design of Sulfur Tolerant Hydrogenation Catalysts, Journal of Catalysis, 2006, vol. 243, pp. 36-42.

Regnier et al., Studies on the Composition of the Essential Oils of Three *Nepeta* Species, Phytochemistry, vol. 6 (1967), pp. 1281-1289.

Regnier et al., Nepetalactone and Epinepetalactnoe From Nepeta cataria, Phytochemistry, vol. 6 (1967), pp. 1271-1280.

Navarro et al., Hydrogenation of Aromatics on Sulfur Resistant PTPD Bimetallic Catalysts, Journal of Catalysis, vol. 189 (2000), pp. 184-194.

Yang et al., Shape Selective and Hydrogen Spillover Approach in the Design of Sulfur Tolerant Hydrogenation Catalysts, Journal of Catalysis, vol. 243, (2006), pp. 36-42.

Tanimori et al., Total Synthesis of (+) Dihydronepetalactone, Agric. Biol. Chem., vol. 55 (1991), pp. 1181-1183.

Fleming et al., Sterocontrol in Organic Synthesis Using Silicon-Containing Compounds, A Synthesis of (+) Dihydronepetalactone Using the Se2 Reaction of an Allysilane, J. Chem. Soc., Perkin Trans., vol. 1 (1998), pp. 2645-2649.

Wolinsky et al., Synthesis of the Dihydronepetalactones, J. Org. Chem., vol. 37 (1972), pp. 3376-3378.

Jefson et al., Chemical Defense of a Rove Beetle, Jounral of Chemical Ecology, vol. 9 (1983), pp. 150-180.

Cavill et al., Defensive and Other Secretions of the Australian Cocktail Ant, *Iridomyrmex nitidiceps*, Tetrahedron, vol. 38 (1982), pp. 1931-1938.

Peterson et al., Insect Repellents—Past, Present and Future, Pesticide Outlook, Aug. 2001.

Depooter et al., The Essential Oils Five *Nepeta* Species, a Preliminary Evaluation of Their Use in Chemotaxonomy by Cluster Analysis, Flavour and Fragrance Journal, vol. 3 (1988), pp. 155-159.

Handjieva et al., Constituents of Essential Oils from Nepeta cataria L., N Grandiflora M.B. and N. nuda L., J. Essential Oil Res., vol. 8 (1996), pp. 639-643.

\* cited by examiner

HYDROGENATION OF CATMINT OIL

This application is a divisional of, and claims the benefit of, U.S. application Ser. No. 14/034,857, filed 24 Sep. 2013, now U.S. Pat. No. 8,952,182; which is a divisional of, and claims the benefit of, U.S. application Ser. No. 12/519,582, filed 19 Nov. 2009, now U.S. Pat. No. 8,552,210; which is the U.S. national stage application of Intl. Application No. PCT/US07/25988, filed 20 Dec. 2007; which claimed the benefit of U.S. Provisional Application No. 60/876,569, filed 21 Dec. 2006; each of which is by this reference incorporated in its entirety as a part hereof for all purposes.

TECHNICAL FIELD

The present invention relates to the hydrogenation of the essential oil of the catmint plant, *Nepeta cateria*. The hydrogenation of the essential oil provides an enriched source of the insect repellent, dihydronepetalactone.

BACKGROUND

Dihydronepetalactone (DHN) has been shown to be an effective insect repellent, as discussed in U.S. Ser. No. 05/112,166. Dihydronepetalactone can be produced by hydrogenating nepetalactone, a component of the essential oil from the catmint plant, *Nepeta cataria* (herein referred to as catmint oil). Catmint oil can be purified from plants of the *N. cataria* by various isolation processes including steam distillation [Regnier, F. E. et al, *Phytochemistry* (1967) 6:1281-1289], organic solvent extraction, microwave-assisted organic solvent extraction, supercritical fluid extraction, mechanical extraction and enfleurage (initial cold extraction into fats followed by organic solvent extraction). The catmint oil so obtained can be used in the crude form to produce DHN, however the hydrogenation reaction can be adversely affected by undesirable components contaminating the crude catmint oil.

Nepetalactone has been purified from catmint oil by crystallization [Regnier, F. E. et al, *Phytochemistry* (1967) 6:1271-1280], however crystallization is expensive, and on the potential scale required for commercialization, it is uneconomical. Therefore, it would be highly desirable to produce a catmint oil with improved properties, such that high yields of the insect repellent DHN may be produced.

SUMMARY

In one embodiment, the processes of this invention provide a process for preparing hydrogenated catmint oil by (a) distilling a beginning amount of crude catmint oil to produce (i) a distillate fraction comprising volatile components driven off from the crude catmint oil, wherein the weight of the distillate fraction comprises about 2% to about 20% of the weight of the beginning amount of crude catmint oil, and (ii) a pot fraction; (b) contacting the pot fraction produced in step (a) with hydrogen and a hydrogenation catalyst to produce hydrogenated catmint oil; and (c) optionally, recovering the hydrogenated catmint oil of step (b).

In another embodiment, the processes of this invention provide a process for preparing hydrogenated catmint oil by (a) distilling a beginning amount of crude catmint oil that has at least about 150 ppm of sulfur-containing compounds to produce (i) a distillate fraction that comprises at least about 8 wt % of the amount of sulfur-containing compounds in the beginning amount of crude catmint oil, and (ii) a pot fraction; (b) contacting the pot fraction produced in step (a) with hydrogen and a hydrogenation catalyst to produce hydrogenated catmint oil; and (c) optionally, recovering the hydrogenated catmint oil of step (b).

In a further embodiment, the processes of this invention provide a process for preparing hydrogenated catmint oil by (a) contacting crude catmint oil with an oxidizing agent to produce a first treated catmint oil; (b) separating the first treated catmint oil from the oxidizing agent to produce a second treated catmint oil; (c) contacting the second treated catmint oil with hydrogen and a hydrogenation catalyst to produce hydrogenated catmint oil; and (d) optionally, recovering the hydrogenated catmint oil.

DETAILED DESCRIPTION

This invention relates to methods for treating the essential oil of the catmint plant, *Nepeta cataria*, herein referred to as catmint oil. The treated catmint oil so produced can be used in a hydrogenation reaction to produce hydrogenated catmint oil, which is enriched in the insect repellent, dihydronepetalactone. Methods for treating catmint oil include distillation and/or treatment with an oxidizing agent.

Definitions:

In the description of the processes hereof, the following definitional structure is provided for certain terminology as employed in various locations in the specification:

The term "nepetalactone" as used herein refers to the compound having the general structure of Formula I:

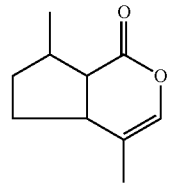

Formula I

The term "dihydronepetalactone" ("DHN") as used herein refers to the compound having the general structure of Formula II:

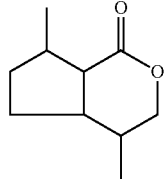

Formula II

The term "puleganic acid" as used herein refers to the compound having the general structure of Formula III:

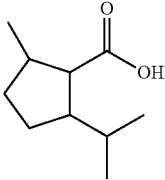

Formula III

The term "nepetalic acid" as used herein refers to the compound having the general structure of Formula IV:

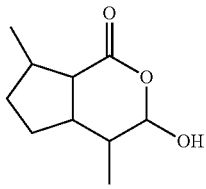

Formula IV

The term "crude catmint oil" as used herein refers to catmint oil that has been obtained from the catmint plant, *N. cataria*, and contains predominantly the trans-cis and/or cis-trans isomers of nepetalactone as shown in Formulae V and VI, respectively.

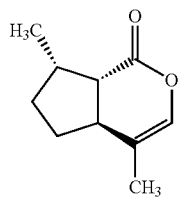

Formula V

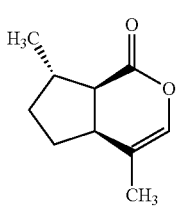

Formula VI

Crude catmint oil may also contain extraneous components such as caryophyllenes, carvones, limonenes and other sesquiterpenes, and other unidentified impurities. One or more of these extraneous components can decrease the effectiveness of the hydrogenation of catmint oil, as measured for example by the rate of conversion of the nepetalactone therein to dihydronepetalactone. The processes of this invention can assist with the removal of one or more of the extraneous components, thereby improving the hydrogenation of catmint oil.

In one embodiment, a process is provided herein for preparing hydrogenated catmint oil by (a) distilling a beginning amount of crude catmint oil to produce (i) a distillate fraction comprising volatile components driven off from the crude catmint oil, wherein the weight of the distillate fraction comprises about 2% to about 20% of the weight of the beginning amount of crude catmint oil, and (ii) a pot fraction; (b) contacting the pot fraction produced in step (a) with hydrogen and a hydrogenation catalyst to produce hydrogenated catmint oil; and (c) optionally, recovering the hydrogenated catmint oil of step (b).

In another embodiment the distillate fraction has about 5% to about 10% by weight of the beginning amount of crude catmint oil.

Depending on the process used to obtain catmint oil from *N. cataria*, the extraneous components contained in catmint oil can comprise sulfur-containing compounds, dimethyl sulfide for example, that may decrease the rate of conversion of nepetalactone, possibly by poisoning the hydrogenation catalyst. Sulfur-containing compounds present in the crude catmint oil can be quantitated using X-ray fluorescence spectroscopy.

In another embodiment, a process is provide herein for preparing hydrogenated catmint oil by (a) distilling a beginning amount of crude catmint oil that has at least about 150 ppm of sulfur-containing compounds to produce (i) a distillate fraction that comprises at least about 8 wt % of the amount of sulfur-containing compounds in the beginning amount of crude catmint oil, and (ii) a pot fraction; (b) contacting the pot fraction produced in step (a) with hydrogen and a hydrogenation catalyst to produce hydrogenated catmint oil; and (c) optionally, recovering the hydrogenated catmint oil of step (b).

In more specific embodiments, the distillate fraction of step (a) comprises at least about 25%, at least about 50% or at least about 75% of the sulfur-containing compounds by weight relative to the beginning amount of sulfur-containing compounds in the crude catmint oil.

Distillation is a well-known process [see, for example, Seader et al, "Distillation", in *Perry's Chemical Engineers' Handbook*, $7^{th}$ Ed. (1997) McGraw-Hill, Section 13]. Distillation methods suitable for the current process include vacuum distillation, steam distillation and solvent distillation. Both steam and solvent distillation can optionally be performed under vacuum. Distillation of crude catmint oil can be carried out using any suitable apparatus, such as a pot or resin kettle outfitted with a heating element, a shell and tube condenser, and a dry ice finger. The temperature at which distillation and condensation occur will depend on the process used. For example, the heating temperature will be lower when vacuum is applied during the distillation process.

When steam distillation is utilized, approximately 2% to about 40% water (by weight relative to the weight of the catmint oil plus the water) may be added to the catmint oil. In a more specific embodiment, approximately 5% to about 20% water (by weight relative to the weight of the catmint oil plus the water) may be added to the catmint oil. In one embodiment, the mixture of catmint oil and water can be distilled at a temperature of about 100° C., i.e. the boiling point of the water, at atmospheric pressure. In an alternative embodiment, the distillation can be performed at an absolute pressure of less than or equal to about 68.9 kPa. In yet another embodiment, the distillation can be performed at an absolute pressure of less than or equal to about 41.4 kPa. At lower pressures, the distillation temperature will be lower due to the lower boiling point of water at reduced pressure.

Solvent distillation refers to a distillation process whereby a solvent is added to aid in the separation of components of close-boiling mixtures. "Close-boiling" mixtures are mixtures wherein the boiling points of the components are similar. In this invention, the solvent used is typically more volatile than the catmint oil, and when distilled off, removes some of the volatile species present in the crude oil. Preferably the solvent is a compound that is inert to the catmint oil. Solvents suitable for this invention include $C_1$ to $C_5$ straight-chain or branched alcohols. In one embodiment, the solvent is an alcohol selected from the group consisting of methanol, ethanol, isopropanol and n-propanol.

Preferably, the initial solvent concentration is from about 5% to about 60% by weight relative to the combined weight of the catmint oil plus the solvent. In another embodiment, the initial solvent concentration is from about 10% to about 25% by weight relative to the combined weight of the catmint oil plus the solvent. Solvent distillation can be performed at atmospheric pressure. In an alternative embodiment, the distillation is performed at an absolute pressure of less than or equal to about 68.9 kPa. In yet another embodiment, the distillation is performed at an absolute pressure of less than or equal to about 41.4 kPa. The temperature at which solvent distillation is carried out will depend on parameters such as the solvent used, the concentration of the solvent, and the pressure at which the distillation is carried out. Typical temperatures range from about 50° C. to about 100° C.

In a further embodiment of this invention, solvent distillation can be combined with steam distillation. For example, one could carry out steam distillation of crude catmint oil as described above to obtain a catmint oil from which some of the volatile components and most of the water have been removed. In a second distillation step, this steam distilled catmint oil is then contacted with a solvent, and solvent distillation is performed as described above. Solvent distillation will remove additional volatile components not removed by steam distillation. In addition, solvent distillation can be used to remove residual water introduced into the catmint oil during steam distillation.

At temperatures above about 80° C., nepetalactone isomers in wet catmint oil may hydrolyze to undesirable products, such as nepetalic acid. The rate of hydrolysis increases with temperature up to about 200° C., where the catmint oil thermally degrades. Therefore, it would be desirable to be able to carry out the distillation of catmint oil at a lower temperature to avoid the hydrolysis of nepetalactone. The temperature can be reduced by operating the distillation apparatus under vacuum. The amount of vacuum applied to the system will depend on the system components, however achieving a vacuum of less than about 68.9 kPa (absolute) is preferred. In one embodiment, vacuum distillation is performed at an absolute pressure of less than about 6.89 kPa.

In an alternative to distillation, a process is provided herein for preparing hydrogenated catmint oil by (a) contacting crude catmint oil with an oxidizing agent to produce a first treated catmint oil; (b) separating the first treated catmint oil from the oxidizing agent to produce a second treated catmint oil; (c) contacting the second treated catmint oil with hydrogen and a hydrogenation catalyst to produce hydrogenated catmint oil; and (d) optionally recovering the hydrogenated catmint oil.

Examples of oxidizing agents suitable for use herein to contact with crude catmint oil include $Na_2B_4O_7 \cdot 10H_2O$, which is available for example in a product such as 20 Mule Team® Borax. In one embodiment, contacting can occur by mixing the catmint oil with $Na_2B_4O_7 \cdot 10H_2O$, followed by filtering the mixture to separate the $Na_2B_4O_7 \cdot 10H_2O$ from the oxidized catmint oil. In an alternative embodiment, the $Na_2B_4O_7 \cdot 10H_2O$ can be placed in a column, and the crude catmint oil can be drained through the column. $Na_2B_4O_7 \cdot 10H_2O$ can be used at a concentration of about 1% to about 50% by weight relative to the combined weight of the $Na_2B_4O_7 \cdot 10H_2O$ plus the catmint oil. In more specific embodiments, $Na_2B_4O_7 \cdot 10H_2O$ can be used at concentrations of about 3% to about 50% and about 15% to about 50% by weight relative to the combined weight of the $Na_2B_4O_7 \cdot 10H_2O$ plus the catmint oil.

Other suitable oxidizing agents for use to contact with crude catmint oil include a hydrogen peroxide solution, which can be used at a concentration of about 1% to about 15% relative to the combined weight of the hydrogen peroxide solution plus the catmint oil. A 30% hydrogen peroxide solution has been found suitable. The mixture of hydrogen peroxide and catmint oil are vigorously agitated, and the aqueous hydrogen peroxide phase is allowed to separate from the organic catmint oil phase. The catmint oil phase can be recovered from the aqueous hydrogen peroxide phase by decantation. Contacting of crude catmint oil with $Na_2B_4O_7 \cdot 10H_2O$ or a dilute hydrogen peroxide solution can be performed at room temperature (about 25° C.).

Ozone is yet another alternative oxidizing agent, which can be used by vigorously agitating the crude catmint oil in the presence of ozone.

In further alternative embodiments, a step of contacting crude catmint oil with an oxidizing agent can be performed before a step of distillation, as described above, is performed.

Crude catmint oil can be obtained from a supplier such as George Thacker Sons (Alberta, Canada), or can be obtained from catmint plant material by known methods, such as distillation [Regnier, F. E. et al, *Phytochemistry* (1967) 6:1281-1289]. One particular method for obtaining catmint oil suitable for use herein includes the steps of (a) contacting *Nepeta cataria* plant material with steam to form a volatilized mixture comprising catmint oil and water; (b) condensing the volatilized mixture formed in step (a) to form a liquid mixture comprising catmint oil and water in which catmint oil is dissolved in water; (c) contacting the liquid mixture formed in step (b) with salt to provide a mixture in which catmint oil and salt are both dissolved in water, and in which
    (i) the solubility of catmint oil in the solution of water and salt is at least about 50% less than the solubility of catmint oil in water, and/or
    (ii) the ratio $[(\rho_{catmint\ oil} - \rho_{aqueous\ solution})/\mu_{aqueous\ solution}]$, where $\rho$ is density, $\mu$ is viscosity and the aqueous solution is the solution of water and salt, is less than or equal to about −0.05,
to provide in the mixture a catmint oil phase that is separated from an aqueous salt solution phase; and (d) recovering the catmint oil phase.

According to this method, plant material is packed into a retort. The lid of the retort is closed and sealed to both the retort and to a condenser. Steam for the distillation of the catmint plant material can be provided by any suitable means. In one embodiment steam is provided to the retort by direct injection through an injection manifold. In an alternative embodiment, the steam can be obtained by adding water to the retort, and boiling the water in the presence of the plant material. The latter method is referred to as using a direct fired retort.

The volatized oil that is produced when steam contacts the plant material is ducted, along with the steam, to a condenser. Cooling water, from any suitable water source, flows through the condenser. Its cooling effect allows the steam and catmint oil vapor to condense to form the heterogeneous liquid condensed mixture. The condenser is configured in such a way as to allow gravity to drain the condensed water and catmint oil out of the condenser and into a collection can. The water and catmint oil are ducted into the collection can optionally using internal baffles in such a way as to produce a quiescent zone to allow the oil and water to effectively separate. Typically, the temperature of the condensate is controlled at a modest temperature, approximately 40-60° C., to allow the oil and water to effectively separate in the quiescent zone of the separation can.

The heterogeneous liquid condensed mixture comprising catmint oil and water can then be contacted with salt, such as by allowing the entire mixture to come into contact with salt. In one embodiment, a porous material such as burlap, filter paper, filter cloth (such as cheesecloth), or a fine mesh screen, is placed in a funnel, and the salt is placed on the porous material. The heterogeneous mixture contacts the salt, and flows through the funnel into the collection can. The addition of salt causes the heterogeneous liquid condensed mixture to separate into a catmint oil phase (top phase in the collection can) and an aqueous salt solution phase (bottom phase in the collection can). The catmint oil phase can be recovered by decantation of the top phase. Salts that are suitable for the process include the sulfate, nitrate and phosphate salts of Groups 1 and 2 of the Periodic Table of the Elements.

This method also provides a method for reducing the amount of catmint oil in wastewater by recycling the condensed water phase back to the retort. This method, with or without recycling, can be carried out under vacuum. Vacuum provides the advantage of allowing the distillation process to be operated under reduced temperature. The amount of vacuum applied to the system will depend on the system components, however achieving an absolute pressure of about 70 kPa to about 13 kPa is preferred.

Following distillation and/or contact with an oxidizing agent, the pot fraction containing catmint oil, or the second treated catmint oil, as described above, can be used in a hydrogenation reaction to obtain hydrogenated catmint oil. The hydrogenation reaction may be carried out in the presence of hydrogen at a temperature of about −10° C. to about 200° C. The hydrogen pressure for the reaction is generally from about 0.1 MPa to about 20.7 MPa. The time, temperature, hydrogen pressure and flow rate and feed may be adjusted, according to known principles, to obtain optimal conversion of hydrogenation of catmint oil using a given catalyst. A suitable hydrogenation reaction is that which is described in U.S. Pat. No. 7,067,677 (which is incorporated in its entirety as a part hereof for all purposes). Described therein is the hydrogenation of nepetalactone in the presence of a catalytic metal that is not nickel, platinum or palladium. The process can be carried out at a temperature of about 25° C. to about 250° C. at a hydrogen pressure of about 0.1 MPa to about 20 MPa.

Other suitable processes for making a dihydronepetalactone include a process of (a) contacting, optionally in the presence of a solvent, a mixture comprising trans-cis nepetalactone and cis-trans nepetalactone with at least one first solid hydrogenation catalyst and hydrogen at a first temperature or temperatures until the concentration of trans-cis nepetalactone is reduced by at least 50% by weight of the weight of the trans-cis nepetalactone at the start of the reaction to form a first product mixture; (b) optionally separating the first product mixture from the at least one first solid hydrogenation catalyst to form a separated first product mixture; (c) contacting the first product mixture or separated first product mixture with at least one second solid hydrogenation catalyst and hydrogen at a second temperature or temperatures to form a second product mixture; and (d) separating said second product mixture from step (c) from the at least one first solid hydrogenation catalyst and/or the at least one second solid hydrogenation catalyst. The at least one first solid hydrogenation catalyst and said at least one second solid hydrogenation catalyst are independently selected and comprise catalytic metal selected from elements from the group consisting of iron, ruthenium, rhenium, copper, osmium, cobalt, rhodium, iridium, nickel, palladium, platinum, alloys or compounds thereof; and combinations thereof. In one embodiment, step (a) is performed at a temperature or temperatures of from about 0° C. to about 100° C. In another embodiment, step (c) is performed at a temperature or temperatures of from about 50° C. to about 150° C.

The hydrogenation reaction may be carried out in batch in a single reactor, in sequential batch in a series of reactors, in reaction zones within one or more reactors, or in continuous mode in any of the equipment customarily employed for continuous processes.

Following the hydrogenation reaction, the hydrogenated catmint oil can be recovered from the reaction mixture by known methods of separation, such as decantation or filtration. Dihydronepetalactone can be recovered from the hydrogenated catmint oil, for example, by column chromatography.

The advantageous attributes and effects of the processes hereof may be seen in a series of examples, as described below. The embodiments of these processes on which the examples are based are representative only, and the selection of those embodiments to illustrate the invention does not indicate that materials, conditions, arrangements, approaches, reactants, steps or techniques not described in these examples are not suitable for practicing these processes, or that subject matter not described in these examples is excluded from the scope of the appended claims and equivalents thereof.

EXAMPLES

The following abbreviations are used: GC is gas chromatography; GC-MS is gas chromatography-mass spectrometry; FID is flame ionization detector; NMR is nuclear magnetic resonance; ° C. is degrees Centigrade; MPa is mega Pascal; kPa is kilo Pascal; Pa is Pascal; rpm is revolutions per minute; mL is milliliter; CMO is catmint oil; wt % is weight percent; TOS is time on stream; NPL is nepetalactone; DHN is dihydronepetalactone; h is hour; conc. is concentration; conv. is conversion; temp. is temperature; ° C. is degrees Centigrade; kg is kilogram; XRF is X-ray fluorescence spectroscopy; ppm is parts per million.

Catmint oil, which was extracted by steam distillation of herbaceous material from the catmint *Nepeta cataria*, was obtained from George Thacker Sons (Alberta, Canada). Ethanol, hexanes and isopropanol, sodium chloride, and hydrogen peroxide were obtained from Sigma-Aldrich (St. Louis, Mo.). 20 Mule Team® Borax ($Na_2B_4O_7 \cdot 10H_2O$) was obtained from a grocery store, however $Na_2B_4O_7 \cdot 10H_2O$ is available from Sigma-Aldrich. The catalyst ESCAT 142 (5% Pd/C) was obtained from Engelhard Corp. (Iselin, N.J.).

Determination of Catmint Oil Constituents and the Hydrogenated Compounds Thereof Samples were diluted with an internal standard solution and injected on a DB FFAP column using an HP5890 (Agilent Technologies, Palo Alto, Calif.) GC equipped with a FID detector. The injection and detector temperatures were 250° C. The temperature of the column was linearly ramped from 50° C. to 250° C. for 20 min and held at 250° C. for the duration of the run. A split mode inlet was used. Peak identification and relative response factors of the major components were determined using calibration standards of nepetalactone, dihydronepetalactone, puleganic acid and nepetalic acid.

Determination of Sulfur Content

Sulfur was quantitated using X-ray fluorescence spectroscopy (XRF) (Panalytical model 2400 wavelength dispersive XRF system (Panalytical Inc., Tempe, Ariz.)).

Hydrogenation Reactions

The rate of hydrogenation was measured by conducting a small scale test hydrogenation reaction in a 50 mL stirred batch autoclave reactor charged with a solution of catmint oil and a powdered catalyst, as described below. The reactor was sealed and then flushed and evacuated with nitrogen several times to remove oxygen. These flushes were followed by two rapid flushes with hydrogen to minimize residual nitrogen in the reactor. The reactor was equipped with a magnetically-coupled gas entrainment agitator which was rotated at about 1000 rpm during the reaction. The reactor temperature was controlled either by flowing a propylene glycol/water mixture from a recirculating bath through an external coil, or by use of an external electrical band heater. Hydrogen was continuously fed to the reactor during the course of the run to maintain a specified pressure as hydrogen was consumed by the reaction. Following the reaction, the reactor was cooled via the external cooling coil and vented. Product analysis was conducted by gas chromatography (GC) as described above using 1,2-dibromobenzene as the internal standard added post reaction. Additional reaction conditions and the corresponding reaction profiles showing conversion of nepetalactones to dihydronepetalactones and key byproducts are provided below for the individual examples.

Example 1 (Comparative Example)

Hydrogenation of Nepetalactone in Untreated Catmint Oil (CMO)

The reaction was carried out using ESCAT 142. The catalyst charge was 10 wt % relative to the weight of CMO, the hydrogen pressure was 8.27 MPa, and the CMO concentration was 50 wt % in ethanol. The reaction was carried out at 15° C.

TABLE 1

Hydrogenation of nepetalactone

| TOS (h) | NPL Conv. (wt %) | DHN Yield (wt %) | Puleganic Acid Yield (wt %) | Neptalic Acid Yield (wt %) |
|---|---|---|---|---|
| 0.17 | 1.6 | ** | ** | 5.9 |
| 0.50 | 8.5 | 97.3 | 3.11 | 5.9 |
| 1.00 | 18.2 | 98.3 | 1.8 | 5.9 |
| 1.5 | 38.4 | 98.1 | 1.9 | 6.2 |
| 2.0 | 47.6 | 98.1 | 1.9 | 5.9 |

** too low to accurately measure.

Example 2

Solvent Distillation of Catmint Oil Using 21 wt % Solvent

This example shows the effect of treating crude catmint oil by solvent distillation using ethanol on the rate of hydrogenation of nepetalactone (NPL) to dihydronepetalactone (DHN). Ethanol was added to crude catmint oil to about 21 wt %. The volatiles, including the ethanol, were stripped off using a single stage flash (no distillation column present) at 1.38 kPa (65° C.) for about 30 minutes, at which time no additional volatile components were observed coming overhead (i.e., no additional condensate (using a dry ice trap) was observed). Approximately 6 wt % of the original crude catmint oil was lost overhead in the distillation. The remaining material was used in a hydrogenation test performed as described in Comparative Example 1. Table 2 shows the rate of hydrogenating this treated oil as the NPL conversion as a function of hydrogenation time or time on stream (TOS). After 2 hours of hydrogenation, the conversion of the nepetalactone increased from 47.6% observed in Comparative Example 1 to 82.1% for the catmint oil subjected to solvent distillation. No appreciable increase in the undesired by-products, nepetalic acid and puleganic acid, were observed.

TABLE 2

Hydrogenation of nepetalactone

| TOS (h) | NPL Conv. (wt %) | DHN Yield (wt %) | Puleganic Acid Yield (wt %) | Neptalic Acid Yield (wt %) |
|---|---|---|---|---|
| 0.17 | 29.2 | 98.7 | 1.32 | 5.9 |
| 0.50 | 48.0 | 98.6 | 1.41 | 5.9 |
| 1.00 | 69.3 | 98.2 | 1.83 | 5.9 |
| 1.5 | 78.8 | 97.9 | 2.14 | 6.2 |
| 2.0 | 82.1 | 97.8 | 2.27 | 5.9 |

Example 3

Solvent Distillation of Catmint Oil at 50 wt % Solvent

This example shows the effect of treating crude catmint oil by solvent distillation with ethanol on the rate of hydrogenation of nepetalactone (NPL) to dihydronepetalactone (DHN). Ethanol was added to crude catmint oil to about 50 wt %. This is substantially more than used in Example 2. The volatiles, including the ethanol, were stripped off using a single stage flash at 7.58 kPa (65° C.) for about 30 minutes, at which time no additional volatile components were observed coming overhead. Approximately 1 wt % of the original crude catmint oil was lost overhead in the distillation. The remaining material was used in a hydrogenation test performed as described in Comparative Example 1. Table 3 shows the rate of hydrogenating this treated oil as the NPL conversion as a function of hydrogenation time or time on stream (TOS). After 2 hours of hydrogenation, the conversion of the nepetalactone increased from 47.6% observed in Comparative Example 1 to 83.5% for the solvent distilled oil. This was done with no apparent increase in nepetalic acid or yield loss to puleganic acid. The crude catmint oil had an initial sulfur content of 278 ppm; the content of the sulfur in the sample used for hydrogenation was 215 ppm.

TABLE 3

Hydrogenation of nepetalactone

| TOS (h) | NPL Conv. (wt %) | DHN Yield (wt %) | Puleganic Acid Yield (wt %) | Neptalic Acid Yield (wt %) |
|---|---|---|---|---|
| 0.17 | 20.3 | 96.8 | 3.7 | 6.1 |
| 0.50 | 42.4 | 99.5 | 0.6 | 6.1 |
| 1.00 | 60.6 | 97.8 | 2.4 | 6.1 |
| 1.5 | 76.3 | 97.6 | 2.6 | 5.8 |
| 2.0 | 83.5 | 97.4 | 2.8 | 6.2 |

Example 4

Steam Distillation of Catmint Oil, Followed by Distillation with Isopropanol

This example shows the effect of treating crude catmint oil by steam distillation, followed by distillation with isopropanol on the rate of hydrogenation of nepetalactone (NPL) to DHN. Catmint oil (2400 grams; Lot 2003 from George Thacker Sons) and deionized water (1440 grams) were combined in a 4 liter heated resin kettle outfitted with a shell and tube condenser and a dry ice cold finger. This resin kettle was outfitted with a vacuum control. Vacuum was controlled at a pressure of 6.9 kPa while the kettle was heated using an electrical heating mantel. The temperature of the water and catmint oil was controlled at 39 to 45° C. Water and some of the catmint oil was stripped off, condensed using the shell and tube condenser and the cold finger and periodically drained from the condenser receiver. After about 7 hours, most of the water was distilled off and a total of approximately 400 mL of isopropanol was added to the catmint oil remaining in the resin kettle. The distillation was continued at about 6.9 kPa but the temperature of the catmint oil/isopropanol mixture was raised to 72 to 80° C. to facilitate the distillation. The distillation was carried out for an additional hour. For the last 10 to 15 minutes, the vacuum was adjusted to 752 Pa to help drive off any residual isopropanol. About 4.5 wt % of the initial charge of the oil was distilled off in this fashion. A total of 7 distillations were performed in this fashion and the distilled catmint oil obtained from the distillations was combined to give a total of about 14.7 Kg of distilled catmint oil. A small portion was used in a hydrogenation test performed as described in Comparative Example 1. Table 4 shows the rate of hydrogenating this treated oil as the NPL conversion as a function of hydrogenation time or time on stream (TOS). After 1.75 hours of hydrogenation, the conversion of the nepetalactone was 82.2%, which is substantially higher than the conversion at approximately the same time in Example 1. This was done with no apparent increase in nepetalic acid or yield loss to puleganic acid. The crude catmint oil had an initial sulfur content of 278 ppm; the content of the sulfur in the sample used for hydrogenation was 205 ppm.

TABLE 4

Hydrogenation of nepetalactone

| TOS (h) | NPL Conv. (wt %) | DHN Yield (wt %) | Puleganic Acid Yield (wt %) | Neptalic Acid Yield (wt %) |
|---|---|---|---|---|
| 0.17 | 16.02 | 99.36 | 0.66 | 6.51 |
| 0.5 | 50.17 | 98.17 | 1.88 | 6.60 |
| 1 | 74.31 | 97.81 | 2.22 | 6.40 |
| 1.75 | 82.19 | 97.11 | 2.86 | 6.66 |
| 2.75 | 84.47 | 97.53 | 2.52 | 6.45 |

Examples 5-11

Hydrogenation of Nepetalactone

Examples 5 through 11 illustrate the hydrogenation of nepetalactone in catmint oil, where the crude catmint oil was treated as indicated.

The hydrogenation reactions were carried out using the catalyst ESCAT 142. The catalyst charge was 10 wt % relative to the weight of the catmint oil, the hydrogen pressure was 3.45 MPa, and the CMO concentration was 50 wt % in ethanol. The reactions were carried out at 25° C. The results are summarized in Table 5.

Example 5 is a Comparative Example for the hydrogenation rate of nepetalactone in untreated catmint oil to dihydronepetalactone.

For Example 6, crude CMO was treated by solvent distillation with ethanol. Ethanol was added to crude catmint oil to about 20 wt %. The volatiles, including the ethanol, were stripped off using a single stage flash at approximately 6.895 kPa (65° C.) for about 30 minutes, at which time no additional volatile components were observed coming overhead. Approximately 6 wt % of the original crude catmint oil was lost overhead in the distillation. The remaining material was used in a hydrogenation test performed as described above.

For Example 7, crude CMO was treated by solvent distillation with ethanol. Ethanol (100 grams) was added to 300 grams of crude catmint oil. The volatiles, including the ethanol, were stripped off using a single stage flash at approximately 6.895 kPa to about 448 Pa (60° C.) for about 30 minutes, at which time no additional volatile components were observed coming overhead. Approximately 4.5 grams of the original crude catmint oil was lost overhead in the distillation. The remaining material was used in a hydrogenation test performed as described above.

For Example 8, crude CMO was treated by contacting it with a dilute hydrogen peroxide solution. A 30% solution of $H_2O_2$ (12 grams) was diluted with 108 grams of deionized water, and this solution was mixed with 120 grams of crude CMO plus 8.5 grams of sodium chloride. The resulting mixture was shaken vigorously in a separatory funnel. The aqueous layer was removed, and the treated CMO was dried and filtered over 10 grams of 13× molecular sieves from Sigma-Aldrich (St. Louis, Mo.). This treatment yielded 108 grams of treated CMO. This material was used in a hydrogenation test performed as described above.

For Example 9, crude CMO was treated by contacting it with a fixed bed of Borax (20 Mule Team® Borax). Glass wool was placed in the bottom of a glass column. Borax (50 grams) was loaded into this column. Crude CMO (142.4 grams) was drained through this column. This treatment yielded 111 grams of treated CMO. This material was used in a hydrogenation test performed as described above.

For Example 10, crude CMO was distilled under high vacuum of 15 to 25 torr absolute. Crude CMO (19.05 kg) was charged to the distillation pot. This distillation was run under a vacuum of 25 to 15 torr. The pot temperature was increased from 120° C. to a final temperature of 147° C. Volatiles were collected from a dry ice cold finger. Seven fractions of distillate (8.34 kg) were collected. The third fraction was used in a hydrogenation test performed as described above. The crude catmint oil had an initial sulfur content of 278 ppm; the content of the sulfur in the third fraction used for hydrogenation was 49 ppm.

TABLE 5

Hydrogenation of nepetalactone

| TOS (h) | Example 5: Comparative Untreated CMO NPL conversion (wt %) | Example 6: 20% ethanol distilled CMO NPL conversion (wt %) | Example 7: 50% ethanol distilled CMO NPL conversion (wt %) | Example 8: $H_2O_2$ treated oil NPL conversion (wt %) | Example 9: Borax treated oil NPL conversion (wt %) | Example 10: High vacuum (closed path) distilled oil NPL conversion (wt %) |
|---|---|---|---|---|---|---|
| 0.08 | 5.3 | 22.4 | 18.7 | 38.9 | 3.0 | 42.2 |
| 0.25 | 13.9 | 55.4 | 40.5 | 79.3 | 29.8 | 74.5 |
| 0.50 | 27.9 | 76.8 | 58.0 | 88.0 | 60.1 | 83.3 |
| 1.00 | 46.9 | 84.3 | 70.5 | 92.8 | 76.8 | 87.6 |
| 2.00 | 65.3 | 89.1 | 78.6 | 97.0 | 83.9 | 92.3 |
| DHN yield at 2 h (wt %) | 98.3 | 94.9 | 97.7 | 94.5 | 98.3 | 97.0 |

For Example 11, crude CMO was contacted with an oxidizing agent. Hydrogen peroxide (30% solution; 50 grams) was mixed with 450 grams of deionized water. This mixture (500 grams) was combined with 51 grams of sodium chloride and 500 grams of crude catmint oil having a sulfur content of approximately 592 ppm. This mixture was vigorously agitated in a separatory funnel, allowed to settle, and then the aqueous phase was separated from the organic phase by decantation. The organic phase was dried over 13× mole sieves, and 467.4 grams of catmint oil was recovered. The sulfur content of this dried peroxide treated oil was 252 ppm. This represents a 57% reduction in sulfur content of the oil. A sample of this treated oil was used in a hydrogenation test performed as described above.

The results are shown in the Table 6. The $H_2O_2$ treated oil showed substantially increase conversion of the nepetalactone after 2 hours of hydrogenation (83.7% versus 25.4% for the untreated oil).

TABLE 6

HYdrogenation of catmint oil

| TOS (h) | NPL Conv. Untreated (wt. %) | NPL Conv. $H_2O_2$-treated (wt. %) |
|---|---|---|
| 0.25 | 3.2 | 42.0 |
| 0.50 | 7.4 | 62.4 |
| 1.00 | 15.3 | 77.1 |
| 2.00 | 25.4 | 83.7 |

Example 12

Steam Distillation of Catmint Oil

This example shows the effect of treating crude catmint oil by steam distillation on the rate of hydrogenation of nepetalactone (NPL) to DHN. Crude catmint oil (705 grams) plus 400 grams of water were loaded into a 4 liter resin kettle outfitted with a condenser. The resin kettle was heated to its boiling point at atmospheric pressure for 4 hours. Some of the water and oil were distilled overhead and condensed. Water (136 grams) and 30 grams of organics (by phase weight) were collected in the distillate receiver. The remaining catmint oil in the resin kettle was decanted from the water phase and used in a hydrogenation test. Table 6 shows the rate of hydrogenating this treated oil as the NPL conversion as a function of hydrogenation time or time on stream (TOS). After 2 hours of hydrogenation, the conversion of the nepetalactone was 89.2% for this steam distilled oil. The data from Table 7 can be compared to the data from Table 8 in Example 13 for untreated catmint oil.

Hydrogenation Conditions:

The reaction was carried out using the catalyst ESCAT 142. The catalyst charge was 10 wt % relative to the weight of the catmint oil, the hydrogen pressure was 0.21 MPa, and the CMO concentration was 10 wt % in hexane. The reaction was carried out at 25° C.

TABLE 7

Hydrogenation of nepetalactone

| TOS (h) | NPL Conv. (wt %) | DHN Yield (wt %) | Puleganic Acid Yield (wt %) | Neptalic Acid Yield (wt %) |
|---|---|---|---|---|
| 0.17 | 46.5 | ** | ** | 10.2 |
| 0.50 | 80.7 | ~100 | ~0 | 9.7 |
| 1.00 | 86.3 | ~100 | ~0 | 9.0 |
| 1.5 | 87.5 | ~100 | ~0 | 9.8 |
| 2.0 | 89.2 | ~100 | ~0 | 9.5 |

** too low to accurately measure.

Example 13 (Comparative Example)

Hydrogenation of Nepetalactone

Crude catmint oil was hydrogenated under the conditions described in Example 12. For this untreated oil, there was only a 64.8% conversion of the NPL after 2 hours.

TABLE 8

Hydrogenation of nepetalactone

| TOS (h) | NPL Conv. (wt %) | DHN Yield (wt %) | Puleganic Acid Yield (wt %) | Neptalic Acid Yield (wt %) |
|---|---|---|---|---|
| 0.17 | 7.3 | 84.9 | ** | 1.11 |
| 0.50 | 23.5 | 94.5 | 4.9 | 1.11 |
| 1.00 | 43.4 | 95.6 | 4.0 | 1.13 |
| 1.5 | 56.3 | 95.4 | 4.2 | 1.13 |
| 2.0 | 64.8 | 95.7 | 4.0 | 1.16 |

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

What is claimed is:

1. A process for preparing hydrogenated catmint oil comprising:
    (a) distilling a beginning amount of crude catmint oil that has at least about 150 ppm of sulfur-containing compounds to produce (i) a distillate fraction that comprises at least about 8 wt % of the amount of sulfur-containing compounds in the beginning amount of crude catmint oil, and (ii) a pot fraction;
    (b) contacting the pot fraction produced in step (a) with hydrogen and a hydrogenation catalyst to produce hydrogenated catmint oil; and
    (c) optionally, recovering the hydrogenated catmint oil of step (b).

2. The process of claim 1 wherein the step of distilling (a) comprises a step of (i) vacuum distilling, (ii) steam distilling, (iii) solvent distilling, or (iv) steam distilling followed by solvent distilling.

3. The process of claim 2 which comprises a step of solvent distilling, or of steam distilling followed by solvent distilling, and wherein, at the beginning of solvent distilling, the weight of the solvent comprises about 5% to about 60% of the combined weight of catmint oil plus solvent.

4. The process of claim 3 wherein, at the beginning of solvent distilling, the weight of the solvent comprises about 10% to about 25% of the combined weight of catmint oil plus solvent.

5. The process of claim 2 which comprises a step of solvent distilling, or of steam distilling followed by solvent distilling, and wherein a solvent comprises a $C_1$ to $C_5$ straight-chain or branched alcohol.

6. The process of claim 2 wherein steam distilling, solvent distilling, or steam distilling followed by solvent distilling, is performed under vacuum.

\* \* \* \* \*